US005637103A

United States Patent [19]

Kerwin et al.

[11] Patent Number: 5,637,103
[45] Date of Patent: Jun. 10, 1997

[54] FLUID COLLECTION AND DISPOSAL SYSTEM

[76] Inventors: Michael J. Kerwin, 11108 Fairborough Ct.; Jacky S. Yam, 1752 Legend La., both of St. Louis, Mo. 63146; Keith G. Korte, 106 E. Main St., Damiansville, Ill. 62215; Theodore J. Klefisch, Jr., 12349 Apt. D, Maverick Dr., Maryland Heights, Mo. 63043; Alan B. Ranford, 40 Patterson Ct., St. Louis, Mo. 63146; Jerry W. Olive, 1572 Greenfield Crossing, Ballwin, Mo. 63021

[21] Appl. No.: 32,946

[22] Filed: Mar. 17, 1993

[51] Int. Cl.$^6$ .................................. B65D 81/00; A61J 1/05
[52] U.S. Cl. .................. 604/317; 134/150; 134/166 R; 134/169 R
[58] Field of Search .................... 588/258, 900; 604/317–326; 134/150, 166, 169; 422/300, 302

[56] References Cited

U.S. PATENT DOCUMENTS

| Re. 30,097 | 9/1979 | Gillespie | 222/651 X |
|---|---|---|---|
| 2,312,950 | 3/1943 | Zimarik | 68/17 R |
| 2,647,384 | 8/1953 | Erlanger | 68/17 R |
| 2,936,757 | 5/1960 | Trace | 604/321 |
| 3,014,481 | 12/1961 | Rumble, Jr. et al. | 604/245 |
| 3,044,285 | 7/1962 | Koplin | 68/12 |
| 3,075,524 | 1/1963 | Clark, Jr. | 422/113 |
| 3,139,238 | 6/1964 | Norstrud et al. | 239/210 |
| 3,163,149 | 12/1964 | Ivey | 134/95 X |
| 3,191,600 | 6/1965 | Everett | 604/319 |
| 3,435,834 | 4/1969 | Cooper . | |
| 3,543,752 | 12/1970 | Hesse et al. | 604/127 |
| 3,578,774 | 5/1971 | McDonald, Jr. | 604/67 |
| 3,645,283 | 2/1972 | Cassells . | |
| 3,672,391 | 6/1972 | Livingston et al. | 134/171 X |
| 3,707,160 | 12/1972 | Query | 134/95 X |
| 3,799,396 | 3/1974 | Ashmead et al. | 222/134 |
| 3,802,447 | 4/1974 | Bender . | |
| 3,804,297 | 4/1974 | Jurjans | 68/17 R X |
| 3,833,417 | 9/1974 | Griparis . | |
| 3,881,328 | 5/1975 | Kleimola et al. | 134/95 X |
| 3,896,827 | 7/1975 | Robinson | 134/56 D X |
| 3,901,408 | 8/1975 | Boden et al. | 222/134 |
| 3,916,924 | 11/1975 | McGowan | 134/95 |
| 3,929,133 | 12/1975 | Ragab | 604/319 |
| 4,090,502 | 5/1978 | Tajika | 604/30 |
| 4,105,031 | 8/1978 | Kurtz et al. | 604/321 |
| 4,135,515 | 1/1979 | Muriot | 128/276 |
| 4,213,796 | 7/1980 | Schaffer | 134/95 X |
| 4,244,364 | 1/1981 | Grushkin | 128/214 E |
| 4,275,726 | 6/1981 | Schael | 128/213 A |
| 4,277,290 | 7/1981 | Andrews et al. | 134/95 X |
| 4,287,867 | 9/1981 | Du Toit | 128/66 |
| 4,306,557 | 12/1981 | North | 604/319 |
| 4,307,741 | 12/1981 | Rossi | 134/100 |
| 4,312,463 | 1/1982 | Daby | 222/134 |
| 4,319,568 | 3/1982 | Tregoning | 128/214 F |
| 4,417,891 | 11/1983 | Cianci | 604/317 |
| 4,449,976 | 5/1984 | Kamen | 604/254 |

(List continued on next page.)

FOREIGN PATENT DOCUMENTS 3805609  9/1993  Germany .

OTHER PUBLICATIONS

John M. Hyde, New Developments in CIP Practices, Jan. 1985, pp. 39–41.

*Primary Examiner*—Robert A. Clarke
*Attorney, Agent, or Firm*—Montgomery W. Smith; Ari M. Bai; Grant D. Kang

[57] ABSTRACT

A fluid collection and disposal system which includes a reusable collection unit designed to operate in conjunction with a disposable manifold for collecting fluids aspirated from a patient during a surgical procedure, and to be cleaned by a servicing unit after use. The servicing unit removes the collected fluid from the collection unit and prepares it for reuse. The disposable manifold is removed from the collection unit prior to its attachment to the servicing unit, and a new disposable manifold is replaced on the collection unit after servicing.

44 Claims, 5 Drawing Sheets

U.S. PATENT DOCUMENTS

| | | | |
|---|---|---|---|
| 4,493,695 | 1/1985 | Cook | 604/27 |
| 4,540,413 | 9/1985 | Russo | 604/320 |
| 4,626,248 | 12/1986 | Scheller | 604/319 |
| 4,627,833 | 12/1986 | Cook | 604/34 |
| 4,642,093 | 2/1987 | Härle | 604/404 |
| 4,646,786 | 3/1987 | Tanaka et al. | 134/172 X |
| 4,653,010 | 3/1987 | Figler et al. | 222/134 |
| 4,687,121 | 8/1987 | Copeland | 68/17 R X |
| 4,832,689 | 5/1989 | Mauerer et al. | 604/67 |
| 4,863,446 | 9/1989 | Parker | 604/317 |
| 4,905,325 | 3/1990 | Colditz . | |
| 4,915,119 | 4/1990 | Franklin | 134/57 R |
| 4,955,391 | 9/1990 | Parker et al. | 128/771 |
| 4,957,491 | 9/1990 | Parker | 604/317 |
| 5,135,485 | 8/1992 | Cohen et al. | 604/67 |
| 5,242,435 | 9/1993 | Terry | 604/317 |
| 5,449,009 | 9/1995 | Kerwin et al. | 134/169 R |

1

FLUID COLLECTION AND DISPOSAL SYSTEM

BACKGROUND OF THE INVENTION

1. Field of the Invention

This invention relates to fluid disposal systems. More particularly, this invention relates to a system for disposing of body fluids and irrigants collected during surgical procedures.

2. Prior Art

The safe and convenient disposal of fluids collected during a surgical procedure in a manner which causes a minimal environmental impact has long been a difficult problem in the medical care industry. Presently, disposable suction canisters are used to collect body fluids during surgical procedures. Setup, use, handling and disposal of prior art suction canisters is often difficult and can place the health care workers and housekeeping personnel at risk of infection. For example, prior art procedures often include opening used canisters to dump the fluid into the sanitary sewer. This however is becoming an unacceptable risk to medical housekeeping personnel. Also, the prior art practice of incinerating the canisters, either after they have been emptied or with the collected fluid remaining therein, is becoming an environmentally undesirable alternative.

Completely reusable fluid collection and disposal systems are an alternative to the use of disposable canisters for fluid collection and disposal. A system exemplary of the prior art of this type is shown in U.S. Pat. No. 4,863,446 to Parker. This system includes a collection unit for collecting fluids during a surgical procedure, and a treatment unit for coupling with the collection unit to remove and dispose of the fluids. The treatment unit is designed to couple with the collection unit to provide washing fluid to wash the collection unit and then drain the entire contents of the collection unit into the sanitary sewer. Although the Parker device may overcome several drawbacks of the prior art disposable canisters, it nevertheless has several drawbacks including difficulty in ensuring complete cleaning of the collection unit prior to reuse, difficulty in transporting and maneuvering in the collection unit in the operating room when in use during a surgical procedure, and bulkiness and weight of the collection unit.

There is therefore a need in the art to develop a disposal system which reduces the potential exposure of medical personnel to contaminated or infectious fluids collected during a surgical procedure, and which is also simple and convenient to transport, with the minimal amount of difficulty in servicing the collection unit prior to reuse thereof, which maximizes safety while at the same time minimizing environmental impact.

OBJECTS AND SUMMARY OF THE INVENTION

A principal object of the present invention is to provide a disposal system which safely and conveniently disposes of collected fluids.

Another object of the present invention is to minimize the health care worker's exposure to the collected fluid.

A further object of the present invention is to minimize solid waste disposal.

Another object of the present invention is to provide a disposal system which includes a collection unit which occupies a minimal amount of space in the operating room yet maximizes fluid collection capacity.

Another object of the present invention is to provide a disposal system which includes a servicing unit having an automated control system designed to simplify user operation.

It is further an object of the present invention to provide a system which allows visual verification of proper servicing of a collection unit prior to its reuse.

A further object of the present invention is to provide a disposal system which is simple to set up in the operating room in preparation for an operation.

These and other objects and advantages of the present invention are realized in a presently preformed embodiment thereof which provides for disposal of fluid in a safe and convenient manner by providing a collection unit having minimal size compared to its fluid volume capacity, and a servicing unit therefore which minimizes user exposure to potentially dangerous or infectious fluids.

In a presently preferred embodiment, shown by way of example and not necessarily by way of limitation, a disposal system made in accordance with the principals of the present invention is comprised of a reusable collection unit intended to collect fluids during a surgical procedure, a disposable manifold used in conjunction with the collection unit during collection of fluids, and a servicing unit for cleaning and applying disinfectant to the collection unit in preparation for its reuse.

The collection unit comprises a single collection vessel and site glass surrounded by a mostly transparent housing which allows easy viewing of the vessel, and covered with a vessel lid having a plurality of port openings therethrough for the attachment of the disposable manifold during fluid collection, and alternatively for attachment of the servicing unit thereto for cleaning. The vessel lid is secured to the vessel by a top cover which also includes a handle for convenience in transporting the collection unit.

The disposable manifold includes connection extensions for connection to the vessel lid during fluid collection in the OR. The manifold also includes a plurality of suction inlet ports for attaching suction lines through which fluid from the patient can be collected into the collection unit, and a vacuum outlet port to which a source of vacuum can be attached. The disposable manifold also includes an anti-reflux valve positioned between the suction inlet ports and the vessel which allows pressure balancing between the collection vessel and the site glass, and which prevents fluids from returning to the patient.

The servicing unit is preferably microprocessor controlled to automatically dump the collection unit contents to a sanitary sewer and thoroughly clean and properly apply an intermediate level of disinfectant to the collection unit and service unit fluid pathways. The servicing unit is designed to automatically accept the collection unit in proper position therein for servicing, and automatically lead the system through the proper sequence of events to empty, clean, and apply disinfectant to the collection vessel. Once the service cycle is completed, the servicing unit will allow release of the collection unit therefrom for reuse.

DETAILED DESCRIPTION OF THE PREFERRED EMBODIMENTS

Figure 1:
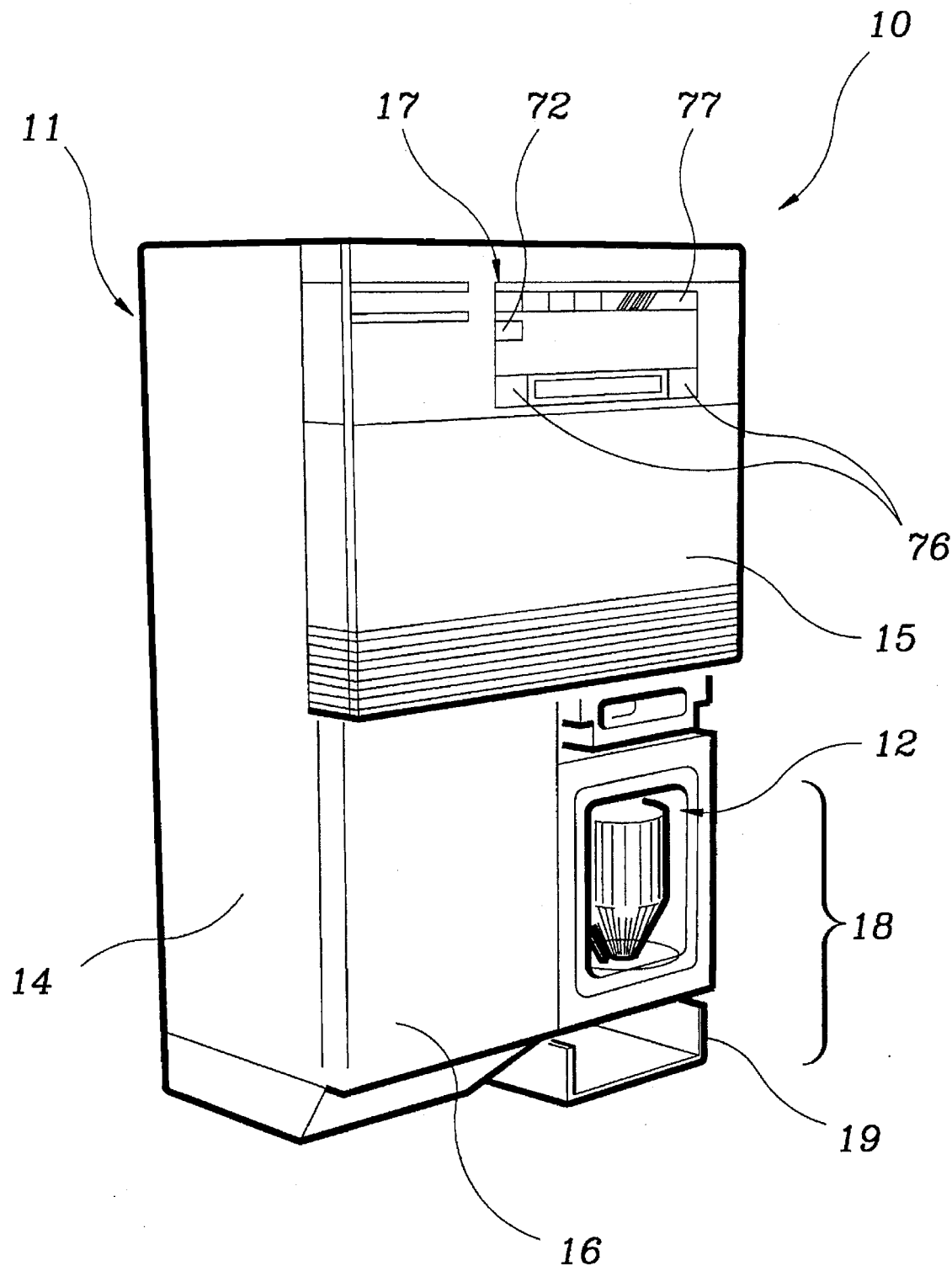
FIG. 1 is a perspective view of the servicing unit portion of the disposal system formed in accordance with the principals of the present invention with a collection unit positioned therein for servicing.

As shown in the exemplary drawings for the purposes of illustration, an embodiment of a disposable system made in accordance with the principals of the present invention, referred to generally by the reference numeral 10, is provided for disposal of fluids collected during a surgical procedure.

Figure 2:
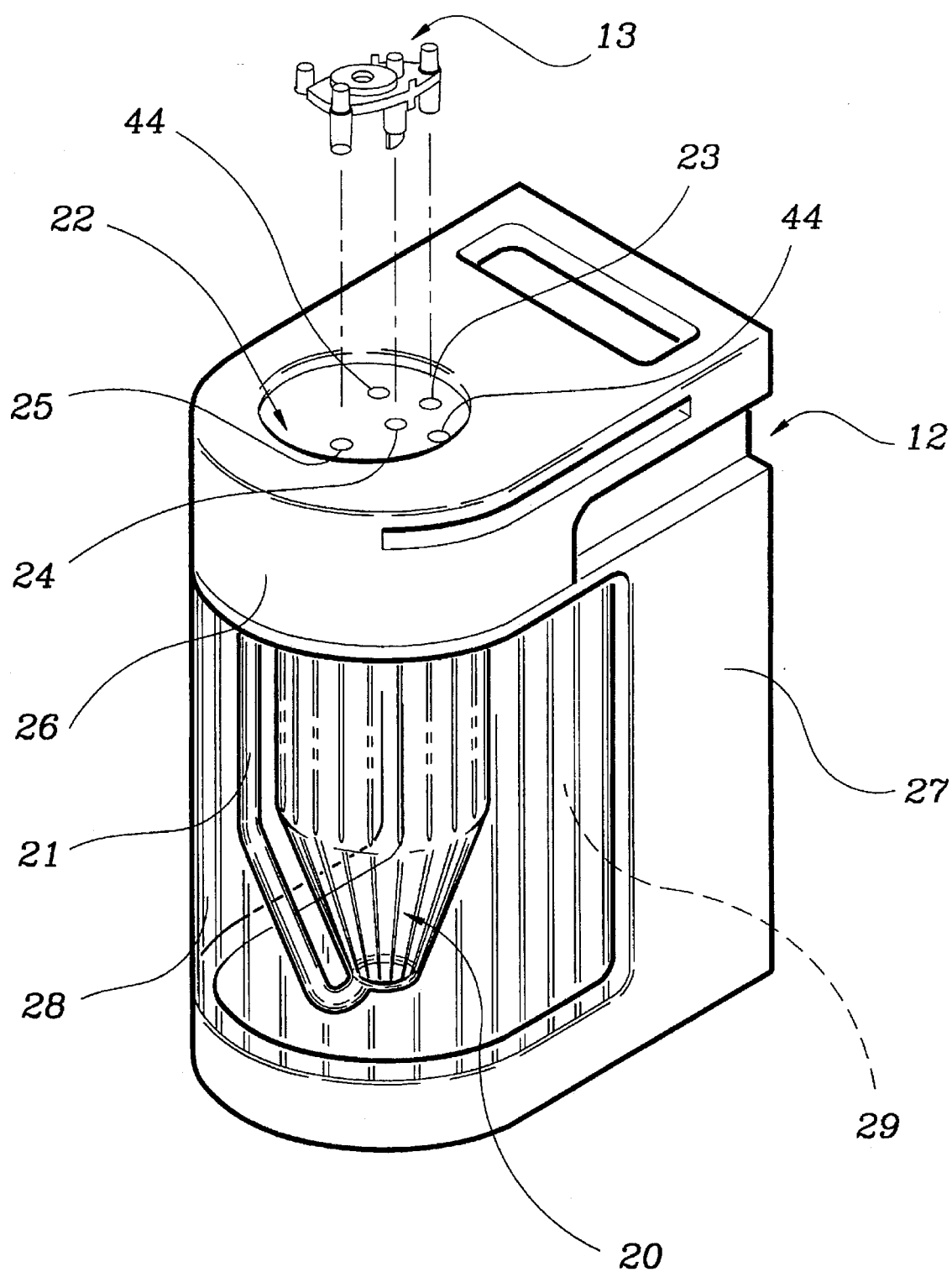
FIG. 2 is a perspective view of the collection unit and disposable manifold portions of the disposal system of the present invention.

More specifically, as shown in FIGS. 1 and 2, the principal components of the disposal system 10 include a servicing unit 11, a collection unit 12, and a disposable manifold 13. The servicing unit 11 comprises a generally rectangular housing 14 having a front panel 15 and a storage door 16. The storage door 16 covers a storage compartment (not shown) suitable for storing quantities of detergent and/or disinfectant. The front panel 15 includes a display 17 which is used to inform the operator of the status of operation of the servicing unit 11. A docking station 18 is also included in the servicing unit 11 which includes a lifting mechanism 19 and which is sized to receive a collection unit 12 for servicing as shown.

Referring now to FIG. 2, the collection unit 12 comprises a vessel 20 which is preferably generally cylindrical in shape with a conically shaped bottom piece. A site glass 21 is preferably formed integrally with the vessel 20 and may have graduated markings thereon or thereabout which indicate the volume of fluid collected in the vessel 20. The top of the vessel 20 is covered with a vessel lid 22 which is preferably slightly concaved on its upper surface to ensure that any unlikely fluid leaks can be contained and to simplify cleaning. The vessel lid 22 includes three openings therethrough which extend into the vessel 20. Each of these openings have a dual function depending on whether fluid is being collected into the vessel 20 during a surgical procedure, or whether the collection unit 12 is being serviced by the servicing unit 11. In the first instance, port 23 operates as the vacuum connection port to supply a source of suction to the vessel 20, the port 24 operates as a patient fluid inlet port through which fluid collected from the patient is drawn by suction into the vessel 20, and port 25 which is in fluid flow connection with the site glass 21 and is closed to the atmosphere during fluid collection.

During servicing of the collection unit 12, the ports 23 and 24 operate as inlet ports for passage of cleaning fluids into the vessel 20, and the port 25 operates as an outlet port to allow collected body fluids, and subsequent cleaning fluids to be withdrawn from the vessel 20 by operation of the servicing unit 11 and disposed of thereby into the sanitary sewer.

The vessel lid 22 is securely held to the vessel 20 by the top cover 26 of the collection unit 12, which itself is secured to the frame 27. The frame 27 surrounds the vessel 20 and includes a transparent optical shield 28 and rear window 29 through which the vessel 20 and the site glass 21 thereof can be easily viewed. The rear window 29 allows backlighting into the collection unit 12 which aids viewing of the contents of the vessel 20 through the transparent optical shield 28 during collection, and aids in viewing the site glass 21 and volume graduation thereon. Referring momentarily to FIG. 1, the rear window 29 also allows viewing of the vessel 20 even when the collection unit 12 is mounted for servicing in the docking station 18 of the servicing unit 11. This allows the operator to visually ensure that the servicing unit is properly performing its service cycle on the collection unit 12 and that the vessel is actually emptied of fluid and appears clean at the end of the servicing cycle.

Figure 3:
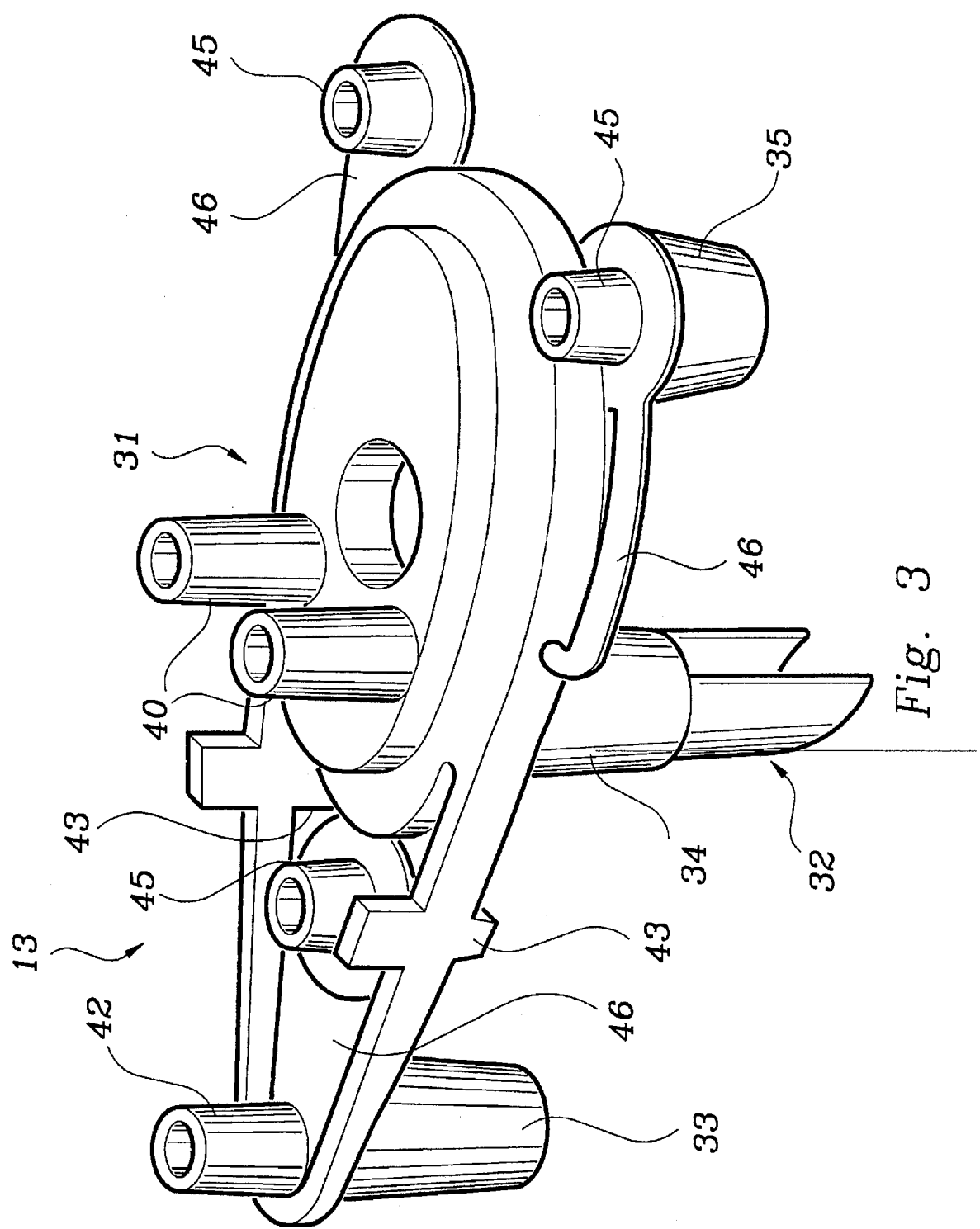
FIG. 3 is a perspective view of the disposable manifold formed in accordance with the principals of the present invention.
Figure 4:
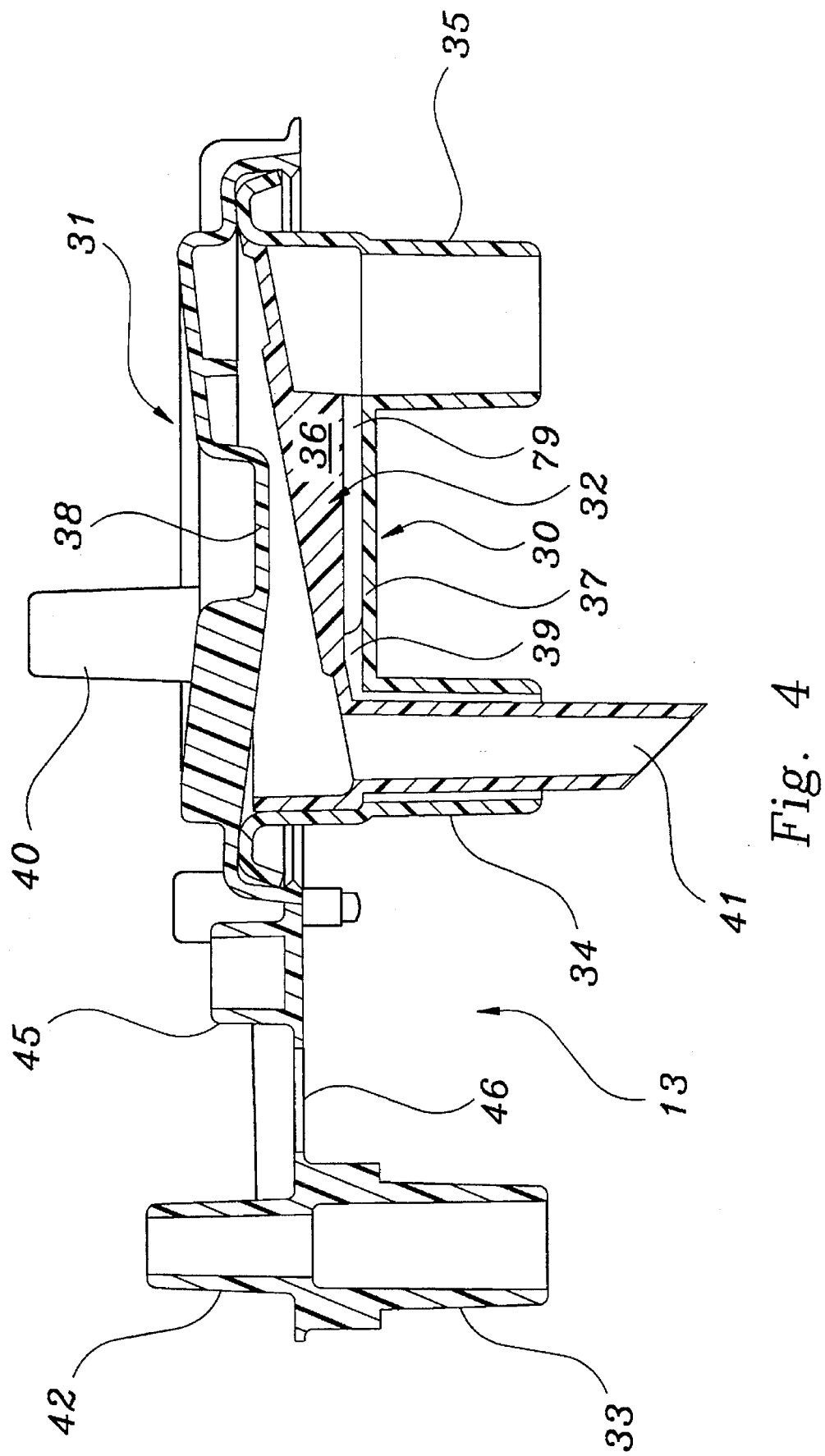
FIG. 4 is a cross-sectional view of the disposable manifold shown in FIG. 3.

The disposable manifold 13 is attached to the collection unit 12 when fluids are being collected from a patient during surgery. As best shown in FIGS. 3 and 4, the manifold 13 is formed from three members, a bottom member 30, a top member 31, and an anti-reflux valve 32. The bottom member 30 includes three lower extensions which are geometrically positioned to be insertable directly into the collection unit ports 23, 24 and 25. These extensions are the vacuum connection extension 33 which is sized to fit within the vacuum connection port 23 of the vessel lid 22, the patient fluid inlet extension 34 which is sized to fit within the patient fluid inlet port 24 of the vessel lid 22, and the site glass extension 35 which is sized to fit within the site glass port 25.

As can be seen, when the manifold 13 is attached to the vessel lid 22, the top of the site glass 21 remains open to the passage of air therebetween and the top of the vessel 20. This is due to the formation of an air channel 39 below the element 36 of the anti-reflux valve 32 by the rib elements 79. The rib element 79 holds the element 36 in a spaced position between the bottom plate 37 and the top plate 38.

The top member 31 of the manifold 13 includes a plurality of suction line connectors 40 to which suction lines can be attached in a well known manner for suctioning fluid from the surgical site into the manifold and through the channel 41 into the vessel 20. A vacuum source connector 42 is positioned in line with vacuum connection extension 33 and allows connection in a well known manner to a vacuum source. The retention latches 43 extend below the top member 31 and are positioned to be received by the retention pins 44 on the vessel lid 22 in a snap fit. The latches 43 ensure that the manifold 13 remains tightly secured to the vessel lid 22 and that the extensions 33, 34 and 35 thereof are held within the ports 23, 24 and 25 respectively in a fluid-tight connection.

The manifold 13 also includes a plurality of caps 45 which are attached to the top member 31 by means of tethers 46 to allow the suction line connectors 40 and the vacuum source connector 42 to be capped off if desired.

Figure 5:
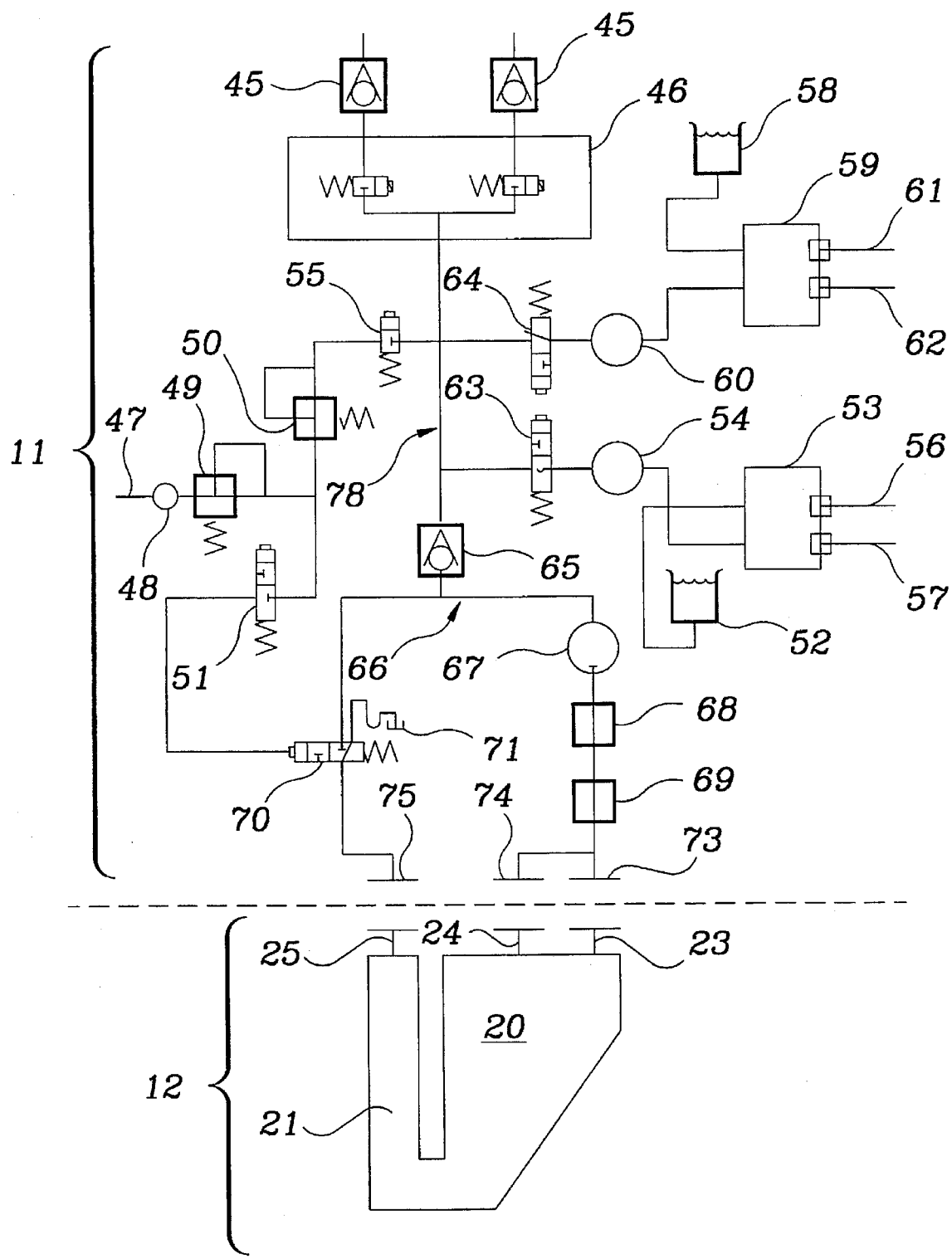
FIG. 5 is a schematic view of the servicing unit and collection unit portions of disposal system of the present invention.

FIG. 5 shows a schematic view of the servicing unit 11 and the collection unit 12. Hot and cold water enter the servicing unit 11 through non-sanitary check valves 45 and pass through a mixing valve 46. Compressed air enters the servicing unit 11 through line 47 and immediately passes through the filter 48 to the compressed air regulator 49. The compressed air branches to pass in a first direction through a second regulator 50 and valve 55, and a second direction through valve 51. Detergent enters the system from detergent reservoir 52 and passes through metering chamber 53 and metering pump 54. The metering chamber 53 includes maximum and minimum level sensors 56 and 57 respectively. The disinfectant enters the servicing unit 11 in a similar manner by passing from disinfectant reservoir 58 through the metering chamber 59 and metering pump 60. The metering chamber 59 also including maximum level and minimum level sensors 61 and 62 respectively. Valves 63 and 64 separate the detergent reservoir and disinfectant reservoir from the main line 78. The sensors signal the microprocessor of the servicing unit 11 which automatically validates delivery of the proper amount of detergent and disinfectant to the main line 78.

Once the cleaning or disinfection fluid moves past the sanitary check valve 65, it enters the sanitary circuit 66. A circulating pump 67, such as a centrifugal pump, is positioned in the sanitary circuit 66 just upstream of pressure sensor 68 and temperature sensor 69. The divert valve 70 is also positioned in the sanitary circuit 66. The divert valve 70, when opened, diverts fluid flow through the sanitary circuit 66 into the sanitary sewer drain 71. Sanitary circuit line extensions 73, 74 and 75 are sized and designed to be insertable into the ports 23, 24 and 25 respectively through the vessel lid 22 in a fluid-tight connection.

System Operation

Operation of the disposal system to effect collection of fluids from a patient and subsequent servicing of the collection unit 12 to thoroughly cleanse the interior of the vessel 20, dispose of the fluids from the vessel 20 to the sanitary sewer, and apply a disinfectant to the interior surfaces of the vessel 20 and the sanitary circuit 66, is explained below.

Prior to use of the collection unit 12 for collecting fluid, a disposable manifold 13 must first be placed in its proper position on the vessel lid 22 in order to connect the ports 23, 24 and 25 with the extensions 33, 34 and 35 respectively in a fluid-tight manner. A vacuum source (not shown) is then connected to the vacuum source connector 42. Next, one or more patient suction lines (not shown) are connected to suction line connectors 40, and unused connectors 40 are closed with caps 45. The collection unit 12 is then ready for use to suction fluids from a surgical site into the vessel 20 thereof.

Fluid from a surgical site is suctioned through suction line connectors 40 and pass down channel 41 of the anti-reflux valve 32 and enter the vessel 20. The anti-reflux valve 32 is made of a very soft material which will collapse and close against pressure in the vessel 20 and thus prevents retrograde movement of fluid through the manifold 13. Air channel 39 operates to ensure pressure equalization between the vessel 20 and the site glass 21, which aids in accurate volume level indication by the site glass 21.

Once fluid collection is completed, the vacuum source is disconnected from the vacuum source connector 42 and the patient suction lines are disconnected from the suction line connectors 40, and the connector 42 and all connectors 40 are closed with caps 45. The collection unit 12 is then transported to the servicing unit 11 with the disposable manifold 13 still in place thereon.

Before the collection unit 12 can be inserted into the servicing unit 11, the disposable manifold 13 must be removed. Referring again to FIG. 1, if a previously processed collection unit 12 has been removed from the servicing unit docking station 18, the docking station 18 should be unobstructed and a "ready" indicator 72 on the display 17 will be activated. The user can then push the collection unit 12 into the service unit docking station 18 until it is completely inserted in the manner shown in FIG. 1. A position detection device (not shown) ensures that the collection unit 12 is properly positioned within the docking station 18 before the lifting mechanism 19 can be activated.

The user then initiates a servicing cycle by pressing two push buttons 76 which are preferably spaced a sufficient distance apart on the display 17, that both of the operator's hands are required for their activation. Upon initiation of the servicing cycle, the collection unit 12 is raised by the lifting mechanism 19 until the sanitary circuit line extensions 73, 74 and 75 (as shown in FIG. 5) of the servicing unit 11 are seated in the ports 23, 24 and 25 respectively of the collection unit 12 in a fluid-tight fit. It is preferred that the operator be required to continue holding both push buttons 76 until the lifting mechanism 19 reaches its maximum height. This is an important safety feature which prevents accidental placement of hands between the servicing unit 11 and the collection unit 12 while the lifting mechanism 19 is in operation. Should the user remove one or both hands from the push buttons 76 before the lifting mechanism 19 has reached its maximum height, movement thereof will stop, and not recommence until both push buttons 76 are again pressed.

Once maximum height is reached, the servicing unit 11 is preferably preprogrammed to allow it to automatically control and complete the remainder of the service cycle unattended by the operator. If a problem in the service cycle is detected by the servicing unit 11, it automatically shuts down servicing operations and signals the operator that a problem has occurred. If desired, the servicing unit microprocessor can be programmed to perform a diagnostic check and download information to the display 17 for assistance to the operator.

Preprogrammed servicing begins by movement of the divert valve 70 to its open position by opening valve 51 to allow compressed air to pass to operate the divert valve 70. Compressed air is then forced through the sanitary circuit 66 into the vessel 20 by opening valve 55, thus forcing fluid therein up the site glass 21 through the port 25 and past the divert valve 70 into the drain 71. Rinse water may then be injected into the vessel 20 and subsequently force into the drain 71 by air pressure.

Pressurized air flow through the sanitary circuit 66 is then stopped by closing valve 55, and the divert valve 70 is then closed by closing valve 51. Water at a predetermined temperature, supplied through mixing valve 46, which may be mixed with a predetermined amount of detergent in the main line 78 by operation of the metering pump 54 and valve 63, is then injected into the sanitary circuit 66 and pumped by pump 67 into the vessel 20 up through the site glass 21 and back into the sanitary circuit 66. The water and detergent are cycled through the sanitary circuit 66 and vessel 20 by pump 67 for a predetermined period of time to insure complete cleansing of the vessel 20, site glass 21 and the entire sanitary circuit 66. The divert valve 70 is then again opened and the fluid is forced by air pressure to the drain 71.

The divert valve 70 is then closed again and water, preferably mixed with a predetermined amount of disinfectant in the main line 78 by operation of the metering pump 60 and valve 64, is injected into the sanitary circuit 66 and continuously cycled for a predetermined period of time. Once disinfection is completed, the divert valve 70 is reopened and the fluid is forced into the drain 71.

The servicing cycle may include any number of preprogrammed ring, wash, disinfect, dry, or other sub cycles as may be desired or necessary for proper servicing of the collection unit 12.

When the service cycle is completed, the "complete" indicator 77 on the display 17 activates. This signals the operator that servicing is complete and the collection unit 12 can be released from the servicing unit 11. The operator then pushes the push buttons 76 to cause the lift mechanism 19 to move to its completely lowered position. The collection unit 12 can then be removed from the servicing unit 11 and the exterior thereof can be wiped down if desired. A new disposable manifold 13 can then be attached to the vessel lid 22 thereof in the manner as described above to complete preparation of the collection unit 12 for reuse in collecting fluids.

It will be apparent from the foregoing that, while a particular embodiment of the invention has been illustrated and described, various modifications can be made thereto without departing from the spirit and scope of the invention. Accordingly, it is not intended that the invention be limited, except as by the appended claims.

We claim:

1. A fluid disposal system comprising:
   collection means for collecting fluid,
   manifold means removably attachable to said collection means for manifolding collected fluid into said collection means; and
   service means for servicing said collection means separate from said manifold means.

2. The fluid disposal system according to claim 1 wherein said servicing means includes means for receiving said collection means.

3. The fluid disposal system according to claim 2 wherein said means for receiving includes a lifting means for lifting said collection means when positioned in said means for receiving said collection means.

4. The fluid disposal system according to claim 1 wherein said manifold means includes manifold extension connectors and said servicing means includes servicing extension connectors, and said collection means includes port means,
   whereby said port means are alternatively connectable with said manifold extension connectors and said servicing extension connectors.

5. The fluid disposal system according to claim 4 wherein said collection means further includes a vessel lid, and said port means are formed in said vessel lid.

6. The fluid disposal system according to claim 4 wherein said port means includes a site glass port which is in fluid flow connection with said site glass.

7. The fluid disposal system according to claim 1 wherein said manifold means also comprises a valve means.

8. The fluid disposal system according to claim 7 wherein said valve means is an anti-reflux valve.

9. The fluid disposal system according to claim 1 wherein said collection means includes a vessel for receiving fluid collected by said collection means.

10. The fluid disposal system according to claim 9 wherein said vessel has a fluid volume of at least five liters.

11. The fluid disposal system according to claim 9 wherein said vessel has a fluid volume of at least 10 liters.

12. The fluid disposal system according to claim 9 wherein said vessel includes a site glass for visually indicating the volume of fluid within said vessel.

13. The fluid disposal system according to claim 12 wherein said site glass also operates as a drain for said vessel.

14. The fluid disposal system according to claim 12 wherein said site glass is integrally formed with said vessel.

15. The fluid disposal system according to claim 9 wherein said vessel is enclosed within said collection means.

16. The fluid disposal system according to claim 15 wherein said vessel is viewable through said collection means.

17. The fluid disposal system according to claim 15 wherein said collection means includes at least one transparent portion through which said vessel can be viewed.

18. The fluid disposal system according to claim 9 wherein said servicing means includes means for attaching said collection means thereto for servicing,
   means for circulating fluid through said collection means which includes means for injecting fluid into said vessel and withdrawing fluid from a site glass.

19. The fluid disposal system according to claim 18 wherein said means for circulating fluid through said collection means includes means for circulating air through said collection means.

20. The fluid disposal system according to claim 18 wherein said means for circulating fluid through said collection means includes means for circulating a predetermined quantity of cleaning fluid through said collection means.

21. The fluid disposal system according to claim 18 wherein said means for circulating fluid through said collection means includes a pump.

22. The fluid disposal system according to claim 18 wherein said means for circulating fluid through said collection means also includes means for diverting fluid therefrom into a drain.

23. A fluid disposal system comprising:
   a collection unit for collecting fluid,
   a manifold removably attachable to said collection unit for manifolding collected fluid into said collection unit; and
   a servicing unit for servicing said collection unit separate from said manifold.

24. The fluid disposal system according to claim 23 wherein said servicing unit includes a docking station for receiving said collection unit.

25. The fluid disposal system according to claim 24 wherein said docking station includes a lifting mechanism for lifting said collection unit when said collection unit is positioned inside said docking station.

26. The fluid disposal system according to claim 23 wherein said manifold includes a manifold extension connectors and said servicing unit includes servicing extension connectors, and said collection unit includes a plurality of ports,
   whereby said plurality of ports are alternatively connectable with said manifold extension connectors and said servicing extension connectors.

27. The fluid disposal system according to claim 26 wherein said collection unit further includes a vessel lid, and said plurality of ports are formed in said vessel lid.

28. The fluid disposal system according to claim 26 wherein said plurality of ports includes a site glass port which is in fluid flow connection with a site glass.

29. The fluid disposal system according to claim 23 wherein said manifold also comprises a valve.

30. The fluid disposal system according to claim 29 wherein said valve is an anti-reflux valve.

31. The fluid disposal system according to claim 23 wherein said collection unit includes a vessel for receiving fluid collected by said collection unit.

32. The fluid disposal system according to claim 31 wherein said vessel has a fluid volume of at least five liters.

33. The fluid disposal system according to claim 31 wherein said vessel has a fluid volume of at least 10 liters.

34. The fluid disposal system according to claim 31 wherein said vessel includes a site glass for visually indicating the volume of fluid within said vessel.

35. The fluid disposal system according to claim 34 wherein said servicing unit includes an means for attaching said servicing unit to said collection unit for servicing, means for circulating fluid through said collection unit which includes an injection means for injecting fluid into said vessel and withdrawing fluid from said site glass.

36. The fluid disposal system according to claim 35 wherein said means for circulating fluid through said collection unit includes means for circulating air through said collection unit.

37. The fluid disposal system according to claim 35 wherein said means for circulating fluid through said collection unit includes means for circulating a predetermined quantity of cleaning fluid through said collection unit.

38. The fluid disposal system according to claim 35 wherein said means for circulating fluid through said collection unit includes a pump.

39. The fluid disposal system according to claim 35 wherein said means for circulating fluid through said collection unit also includes means for diverting fluid therefrom into a drain.

40. The fluid disposal system according to claim 34 wherein said site glass also operates as a drain for said vessel.

41. The fluid disposal system according to claim 34 wherein said site glass is integrally formed with said vessel.

42. The fluid disposal system according to claim 31 wherein said vessel is enclosed within said collection unit.

43. The fluid disposal system according to claim 42 wherein said vessel is viewable through said collection unit.

44. The fluid disposal system according to claim 42 wherein said collection unit includes at least one transparent portion through which said vessel can be viewed.

* * * * *